(12) United States Patent
Grey et al.

(10) Patent No.: US 7,111,756 B2
(45) Date of Patent: Sep. 26, 2006

(54) DOSE DISPENSING APPARATUS

(75) Inventors: Matthew James Grey, New Haw (GB); Martin Philip Riddiford, London (GB); Geoffrey William Guy, Salisbury (GB); Rajiv Bobby Dave, Edgware (GB)

(73) Assignee: GW Pharma Limited, Wiltshire (GB)

( * ) Notice: Subject to any disclaimer, the term of this patent is extended or adjusted under 35 U.S.C. 154(b) by 219 days.

(21) Appl. No.: 10/399,569

(22) PCT Filed: Oct. 22, 2001

(86) PCT No.: PCT/GB01/04689

§ 371 (c)(1),
(2), (4) Date: Oct. 17, 2003

(87) PCT Pub. No.: WO02/32487

PCT Pub. Date: Apr. 25, 2002

(65) Prior Publication Data

US 2004/0069798 A1    Apr. 15, 2004

(30) Foreign Application Priority Data

Oct. 20, 2000   (GB)   ................................. 0025809.5

(51) Int. Cl.
*B67D 5/30*   (2006.01)
*B67D 5/33*   (2006.01)

(52) U.S. Cl. ........................... 222/21; 222/30; 222/36; 222/63; 222/646; 222/153.11

(58) Field of Classification Search ................. 222/14, 222/21, 23, 30, 36, 63, 645, 646, 649, 153.11, 222/402.13

See application file for complete search history.

(56) References Cited

U.S. PATENT DOCUMENTS

| | | | |
|---|---|---|---|
| 5,284,133 A | | 2/1994 | Burns et al. |
| 5,390,238 A | | 2/1995 | Kirk et al. |
| 5,564,414 A | * | 10/1996 | Walker et al. ......... 128/200.23 |
| 5,755,218 A | | 5/1998 | Johansson et al. |
| 5,809,997 A | | 9/1998 | Wolf |

(Continued)

FOREIGN PATENT DOCUMENTS

WO    WO 92/17231 A1    10/1992

(Continued)

*Primary Examiner*—Joseph A. Kaufman
(74) *Attorney, Agent, or Firm*—Wolf, Greenfield & Sacks, P.C.

(57) ABSTRACT

A dispensing system for controlled, especially remote controlled, dispensing of medicaments is disclosed. The system consists of a dispensing mechanism adapted to receive a sealed or resealable container of material to be dispensed and to validate that it is the correct material, and which includes a mechanical actuation mechanism which, when actuated, causes a measured dose of material to be dispensed from the material container. The mechanical actuation mechanism may be inhibited from operation by a locking mechanism which, when actuated, locks the device against the further dispensing of a dose of material until release in accordance with the desired dispensing programme, e.g. until a certain time period has elapsed, or until the programme permits dispensing to occur on some other basis. The dispensing system may be in two parts, a hand-held hand-actuated dispensing mechanism (1) and a base or docking station (2) into which the hand-held unit may be placed in order to release the locking mechanism. The docking or base station (2) may be triggered to cooperate with a remote overall control system, for example a remote computer, by placing the hand-held dispensing mechanism (1) in it.

13 Claims, 5 Drawing Sheets

U.S. PATENT DOCUMENTS 6,234,168 B1 * 5/2001 Bruna .................. 128/203.12
2002/0166871 A1 * 11/2002 Muderlak et al. ............. 222/23

FOREIGN PATENT DOCUMENTS

| WO | WO 00/32097 A1 | 12/1999 |
| WO | WO 01/24690 A2 | 4/2001 |
| WO | WO 01/58236 A2 | 8/2001 |

* cited by examiner

DOSE DISPENSING APPARATUS

RELATED APPLICATIONS

This application is a National Stage application of PCT International Application No. PCT/GB01/04689 filed, Oct. 22, 2001.

BACKGROUND OF INVENTION

This invention relates to dose dispensing apparatus, particularly though not exclusively for dispensing doses of drugs and other like medicaments. It can, however, be used in analogous areas where controlled dispensing of material is desired. It is of particular value for dispensing measured doses of fluent medication from a storage container containing a reservoir of such medication, although it can also be used to dispense unit dosages of solids each as, for example, tablets.

Pharmaceutical packaging is normally designed to make access by the patient easy and unrestricted. There are, however, situations where considerations of safety and security make it necessary to control and record the usage of medicines by patients. Additionally, supervision of dosage by medical, nursing and care staff is time-consuming and costly, particularly if the patient is not in hospital or other care facility. This is especially the case if the patient needs to take a combination of medicines with a strict regime of medication. Also, while in the case of many medicaments and pharmaceuticals the dosage regime may be subject to wide variation without potential danger to the patient on the one hand or loss of effectiveness of the medication on the other, it is well understood that medication is desirably effected using a regular dosage regime. It is found that this is not always easiest achieved simply by relying on a patient to follow written instructions. Attempts have accordingly been made to develop devices which are themselves essentially "programmed" to dispense medicament at the correct intervals, but such systems have tended to be of narrow applicability and complex and, indeed, to be easily defeated. Thus, suggestions have been made in the case of multiple pill-based medication regimes, to provide automated dispensing devices. U.S. Pat. No. 5,752,621 and U.S. Pat. No. 5,472,113 both disclose apparatus which can be used to dispense, at appropriate times, various pills in appropriate combinations. Further prior art dispensing apparatus is referred to in each of these specifications.

Devices for dispensing fluent materials such as drugs and medicaments are known in a wide variety of forms. Generally they consist of a container which is sealed and from which a suitable dose of material may be ejected. One particular widespread presentation for drugs, particularly the treatment of asthma, is that of a small pressurised canister having a valve at one end and a dispensing tube fitted with a nozzle. So-called inhalers are well-known and widely used by asthmatics. In principle, however, such a presentation is not in any sense restricted to drugs for use in treating asthma, but can be used for a wide variety of medicaments and pharmaceuticals. The mode of administration additionally does not always have to be by way of an aerosol spray. For example, it is entirely conceivable to dispense pasty or creamy formulations from a canister with some form of pump valve on it. Even discrete dosage forms such as pills may be presented in containers from which pills may be released one at a time. This is a particularly preferred dosage approach presentation for homeopathic remedies where it is believed highly desirable that the pill may be taken without being handled by the person taking it more than strictly necessary. Alternatively, pills may be incorporated into a strip or ribbon which may be fed out from a cassette or the like one by one, and released from the strip for administration.

A separate consideration in connection with the administration of medicaments arises in the case of controlled clinical trials, or even, though to a lesser extent, patient monitoring. It is particularly important in a controlled clinical trial to ensure not only that the dosage regime is followed, but that a positive record is secured which enables that to be verified. Any such system should, of course, not be capable of being falsified by the patient.

A further separate consideration which applies in some cases is the strong desirability of avoiding overdosing. This can be of particular importance in the case of medicaments used in diabetes treatment where they can have extremely adverse effects if not used in the right quantity at the right time.

Yet a further problem which arises in connection with the controlled administration of medicaments in unsupervised conditions is to ensure that the right medicament is being administered, and in the case of controlled or prescription medicines, that no diversion occurs.

SUMMARY OF INVENTION

We have now found that substantial advantages may be obtained, but in cost-effective fashion, by providing improved dispensing systems which enable a dose of medicament or the like to be dispensed from a sealed or sealable container in accordance with a pre-programmed regime and which are so arranged that the regime must essentially be adhered to.

According generally to a first feature of the present invention, there is provided a dispensing system consisting of a programmable dispensing mechanism adapted to receive a sealed or resealable container containing multiple doses of material to be dispensed, and including a mechanical actuation mechanism which, when actuated, causes a measured dose of material to be dispensed from the material container, and wherein the mechanism may be inhibited from operation by a locking mechanism which, when actuated, locks the device against the further dispensing of a dose of material until released in accordance with a desired dispensing programme, and wherein the container and dispensing mechanism are provided with means enabling the authenticity of the container placed in the dispensing mechanism to be checked.

Such release may be effected, for example, merely by the passage of sufficient time or, and this is generally preferred, by means of the release of a suitable latching mechanism which acts to lock the device against dispensing until such release is effective. The latching mechanism may be mechanical, electrical or electromechanical, but, in every case, must be as a whole programmable with the desired dosage regime. The release may be effected by suitable actuation locally or by remote control.

Preferably the container has an identification tag associated therewith and containing information about its content, and the dispensing mechanism includes means for addressing the tag and validating the dosage regime in accordance with a preset programme. The tag may take the form of a simple marking on the face of the container such as a barcode, or it may be a more sophisticated form of tag including data about the medicament and even being in the form of a "smart card" which enables information not only to be extracted from the tag but also written to the tag.

It is particularly preferred to provide a dispensing system in two parts, one of which can be envisioned as a hand-held hand-actuated dispensing mechanism and the other as a base or docking station into which the hand-held unit may be placed in order to release the latch. Such a docking or base station may be more or less sophisticated and may be self-standing, or alternatively it may operate in cooperation with a remote overall control system, for example a remote computer. In one specific aspect of the present invention, the docking station may contain transmitter/receiver means for communicating with a central control computer enabling exchange of signals/data between the remote computer and the base or docking station and accordingly, if the dispensing device is placed in the base or docking station, between the remote computer and the dispensing device. In such a system, it is entirely possible to arrange by means of suitable programming and suitable easily implemented electronics that the dispensing history of the hand-held device can be uploaded to a central remote computer at the same time or adjacent in time to the remote computer sending the hand-held device appropriate control signals.

The means of communication between a base or docking station and a remote computer can be any appropriate means, for example using cellular telephony techniques, via the Internet or via any other appropriate communications mechanism.

It is also possible to provide, in the hand-held dispensing device, means for communicating with a separate standard computer device, for example a personal computer, palm-top, PDA or WAP telephone. By including an infra-red communications port in the hand-held device, once communication is established by placing the device in or near the docking station and actuating communication, a dialogue may be established between the patient and a host computer or even with a physician or other adviser. Thus, it is possible, at the same time as dealing with the basic reporting of past use of the device, to enable the patient to fill in a questionnaire, or to enter into the system a query about their condition or a report of current state of health. This "telemedicine" aspect to the dispensing system of the present invention provides very substantial flexibility of communication between patient and doctor, and enhances clinical care opportunities.

In the case of clinical trials or similar procedures, operating in this way enables a substantial degree of control and monitoring to be easily and cost-effectively carried out without the ease of use of the medicament for the user or patient being compromised.

BRIEF DESCRIPTION OF THE DRAWINGS

The invention is illustrated by way of example with reference to the accompanying drawings in which.

DETAILED DESCRIPTION

Figure 1:
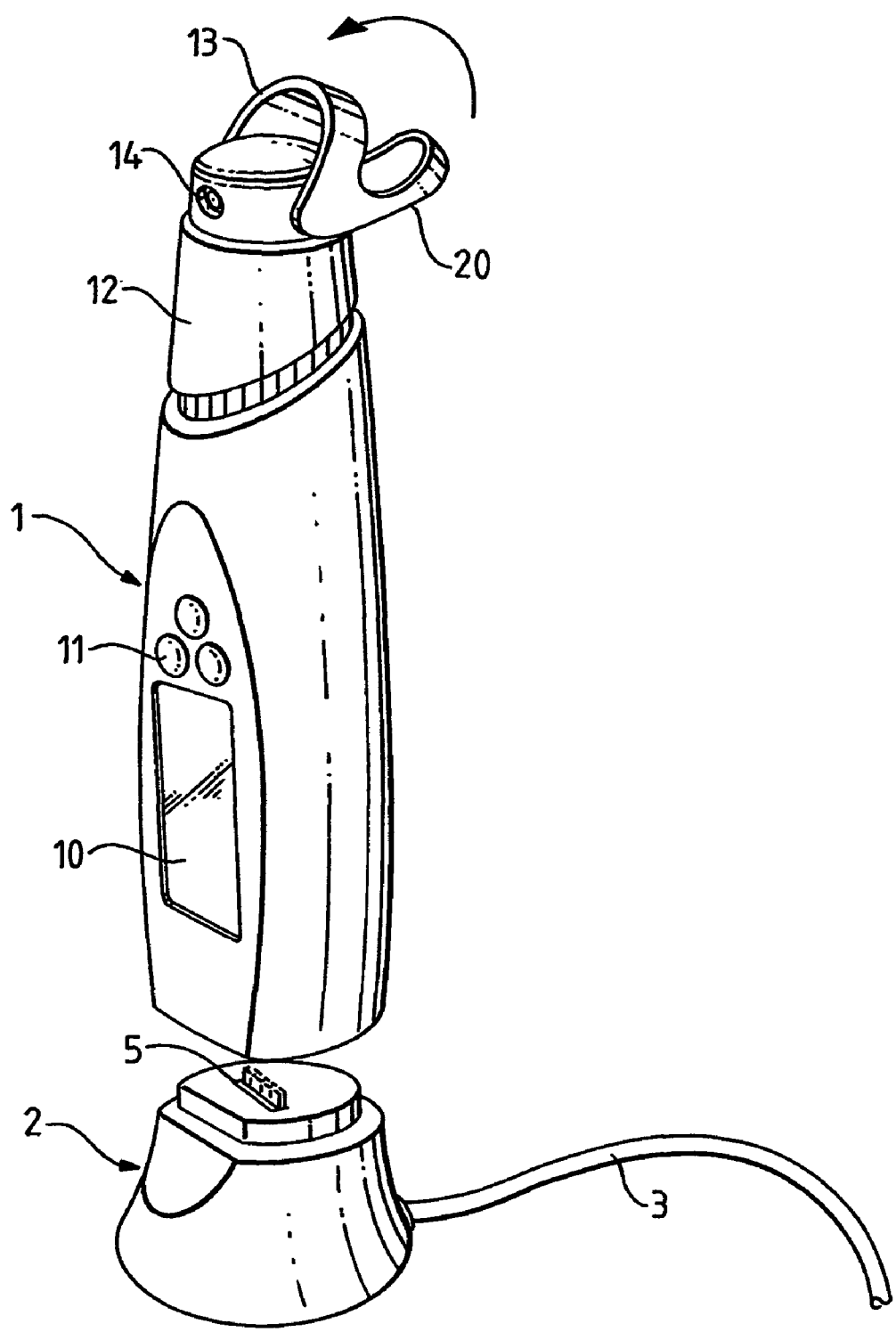
FIG. 1 shows a drug dispensing unit and base station in accordance with the present invention.

Referring to the drawings, FIG. 1 shows a dispensing unit generally denoted 1 which can be placed on top of a base unit generally denoted 2. The base unit is connected via a power and signal cable 3 with appropriate related apparatus, for example to a telephone socket or to a PC interface card. The upper face of the docking station 2 carries a row of connector terminals 5 which can, when the dispensing unit 1 is placed on the docking station 2, electrically contact corresponding members (not shown in FIGS. 1 and 2) located on the underside of the dispensing unit 1.

The dispensing unit itself is provided with a liquid crystal display screen 10 and some function buttons 11, and has at its upper end a nozzle actuation cap 12 with a lowerable closure tab 13 which can be used to cover an aerosol outlet 14 in cap 12, thus preventing the aerosol outlet being clogged with dust, dirt or other contamination.

Cap 12 may be releasable from the upper end of the main body of the dispensing device as shown in the drawings to enable a pressurised canister with a standardised outlet tube to be located within it, the outlet tube being registered with an appropriate aerosol nozzle 14. By pressing the cap 12 down into the main body of dispensing device 1, the aerosol valve may be actuated and a dose of material expelled, whereafter an electromechnical latch within the main body of the dispensing device 1 may act to prevent the cap 12 being pushed into the body of dispensing device 1 a second time until release occurs. Release may occur merely following the passing of a given period of time, but it is highly desirable more positively to control the ability of the device to dispense. For this purpose, it is straightforward to arrange that the latch within the main body of dispensing device 1 will remain locked to prevent a further depression of cap 12 until appropriate steps are taken to release it. For example, release may be effected remotely in accordance with a pre-programmed regime by placing the dispensing unit 1 on to the base station 2 and thereafter having the dispensing station and the base station communicate with one another, whereon, if appropriate, the internal latching may be released. The status of the dispensing device 1 may be shown on screen 10, both before and after placing on the base station. A number of push buttons 11 are provided in order to control input from the user, for example to enable the user to set up a communication link with the remote computer via the base station 2.

Once such a link has been established and e.g. the latch released so that a second dose may be dispensed,. the dispensing device 1 may be removed from the base station, held in the hand as shown in FIG. 2, and the cap again depressed in the direction of arrow 30 shown on FIG. 2. It is easy to arrange that when such actuation occurs, the latch within the dispensing unit 1 re-engages to prevent a second dispensing action and separately the status of dispensing unit may change, the change being displayed in window 10.

Alternatively, the device may include suitable control circuitry internally, such circuitry acting to release locking and enable a further dose to be dispensed after a suitable period of time, and preferably including a rewritable memory store to maintain a record of when doses were in fact administered. The content of such a store may be automatically transferred to a store in the docking station when the device is docked, or transferred direct to a remote computer if desired.

Figure 2:
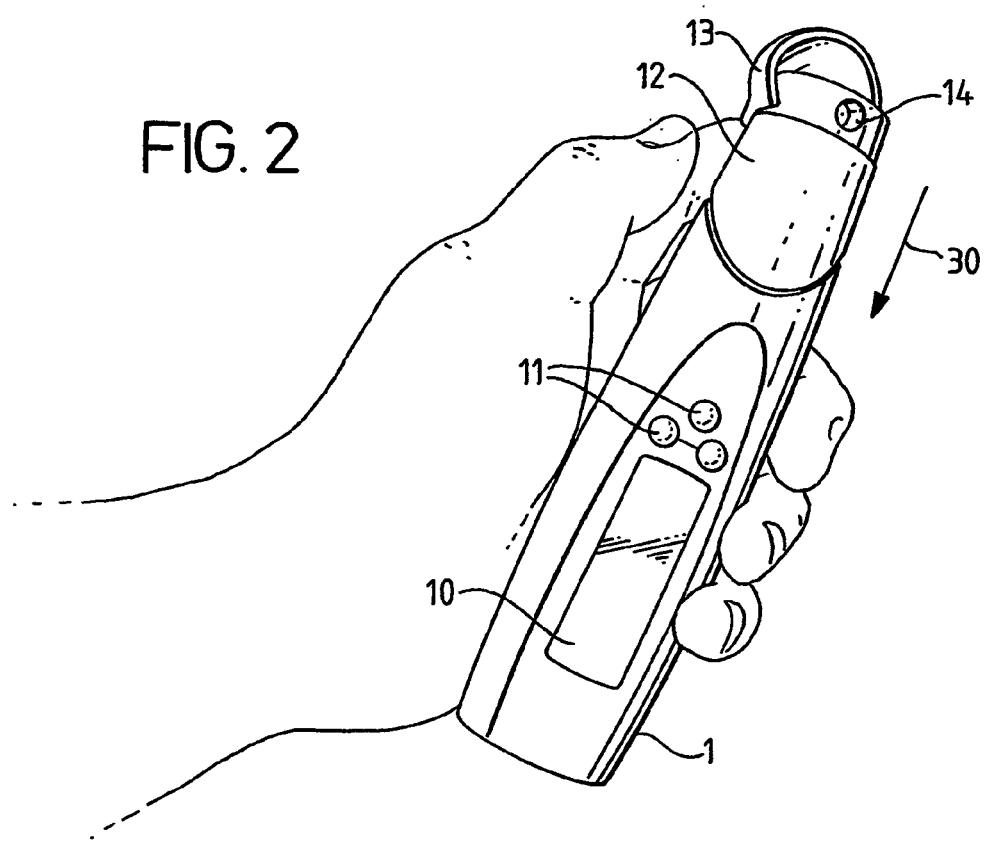
FIG. 2 shows the unit of FIG. 1 about to be used.

As shown in FIG. 1, the closure tab 13 which acts to shield ingress of dirt into the dispensing outlet 14 has an angled out portion 20 which can be engaged by the forefinger of the left hand as shown in FIG. 2 of the drawings in order to achieve dispensing.

Figure 3:
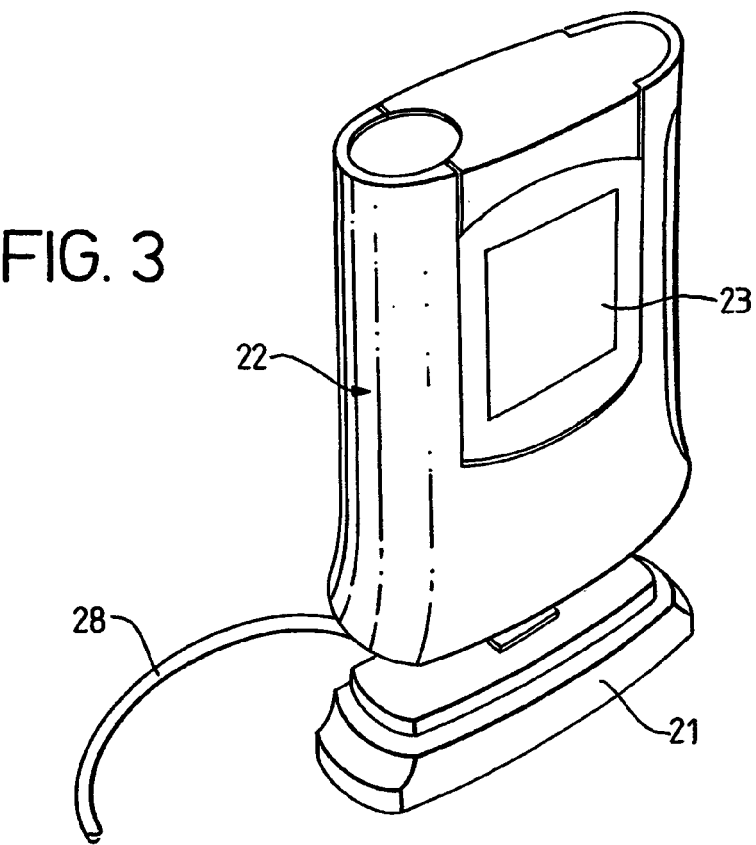
FIG. 3 shows an alternative general view of an alternative dispensing unit and base station.
Figure 4:
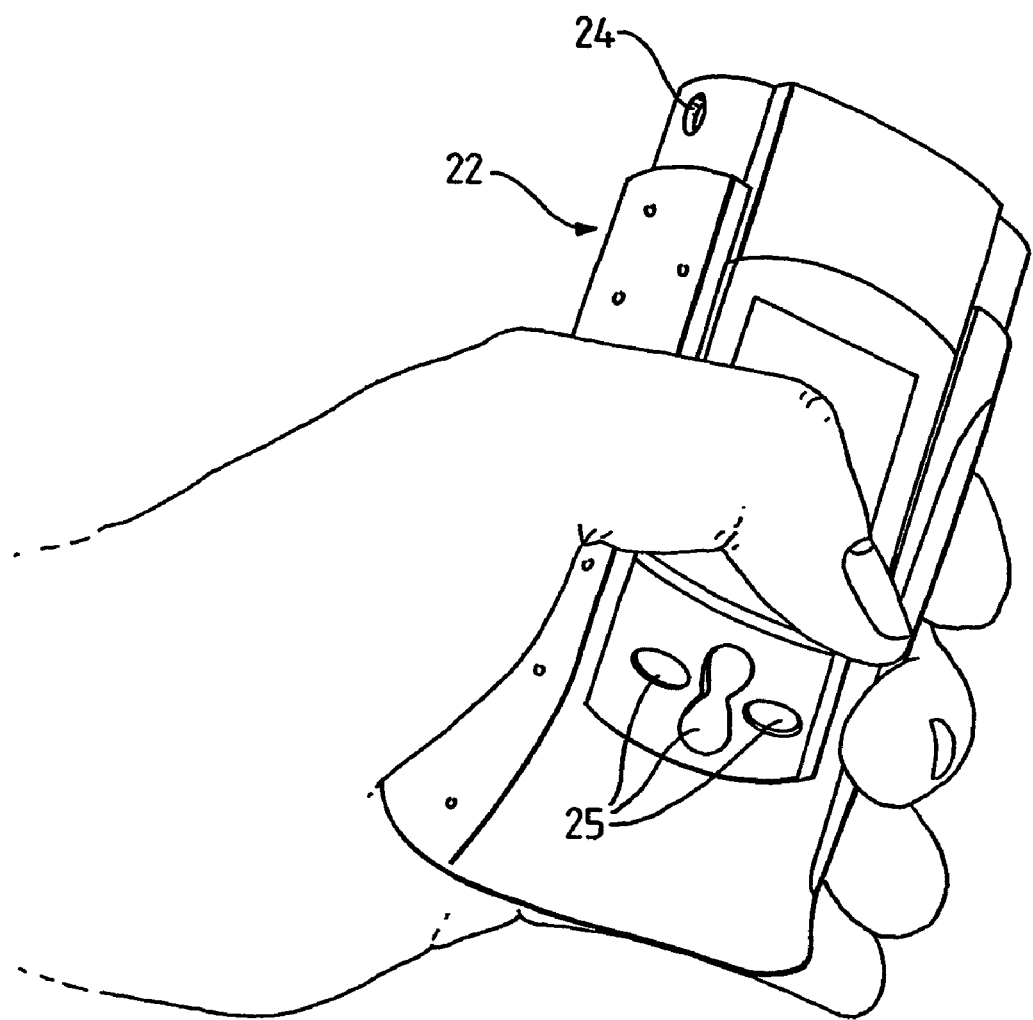
FIG. 4 shows the unit of FIG. 3 in use.

Such an approach is not always desirable, or, indeed, convenient, and it may be particularly awkward for people with arthritis. Accordingly, FIGS. 3 and 4 show an alternative construction where dispensing is achieved by means of a lateral grip across a generally oval cross-section elongate housing which covers the dispensing device. Referring to FIGS. 3 and 4, the system consists again basically of a docking station 21 connected via cable 28 and a squeezable dispensing unit 22. The latter has a display screen 23 in a slidable central section which can be slid up to reveal the nozzle of an aerosol dispensing nozzle 24 which is visible in FIG. 4, but not in FIG. 3. Likewise visible in FIG. 4 but not in FIG. 3 is the set of control buttons 25 which enable the unit to be controlled by the user.

The mechanical construction enabling a squeezing movement exerted as shown in FIG. 4 to be converted into an axial compression to release a dose from a pressurised container via the aerosol nozzle may be simply effected using appropriate standard mechanical constructions, and the mechanical arrangements for latching the device against an immediate second use can likewise be simply and appropriately constructed. Located within the housings of the respective dispensing devices 1 and 22 shown in FIGS. 1 and 3 respectively are also appropriate electronics and a power supply or back-up power supply, for example one or more battery cells. If desired, the electronics may be rechargeable and recharging can take place when the respective dispensing unit is located on its docking station 2 or 21. This can obviously be effected automatically by appropriate design and programming.

Figure 5A:
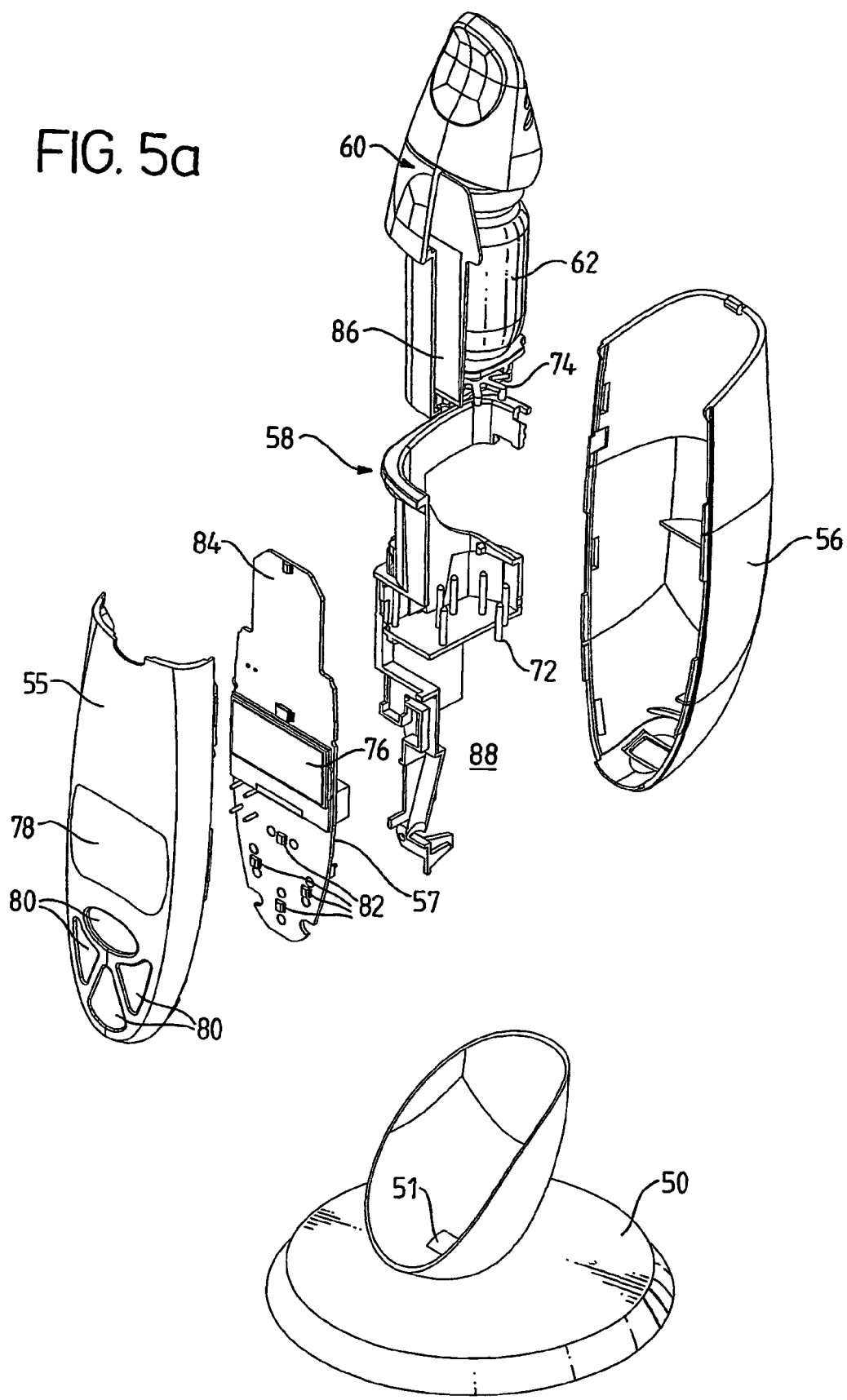
FIGS. 5a and 5b show in exploded view from front and back respectively a third embodiment of a drug-dispensing unit and base station in accordance with the invention.
Figure 5B:
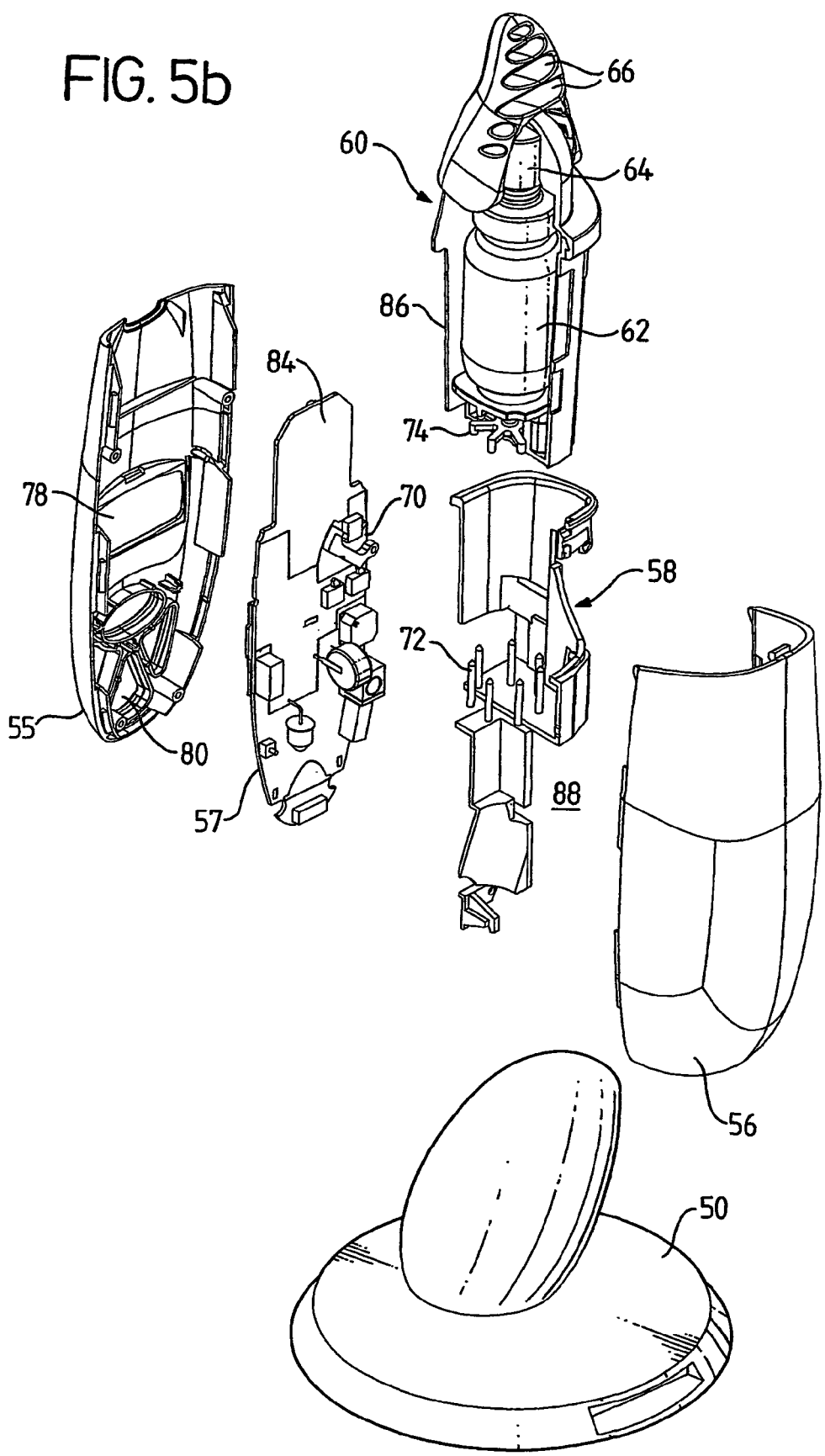

FIGS. 5a and 5b show a further embodiment of the dispensing system, in each case in exploded view from front and back respectively. Referring to these figures, from which detail has been omitted for the sake of clarity, the system consists of a base station 50 into which a hand-held dispenser can be set when needed. A contact pad 51 enables signals to be sent to and from the hand-held unit when it is placed in base station 50.

The hand-held unit consists basically of front and rear casing shells 55,56 respectively which clip together round a circuit board 57 and an internal moulded receptacle unit 58. Shown above unit 58 in the drawing is a removable cartridge housing 60 which may be locked into place in the assembled housing or released therefrom as and when necessary. Cartridge housing 60 is designed to receive a container of medicament 62, here in the form of an aerosol spray canister with a dispensing nozzle 64 which lies in the upper part of housing 60 which is suitably configured to enable a dose of medicament to be dispensed sub-lingually via apertures 66.

Circuit board 57 bears a latch assembly 70 designed to interact with portions of housing 60 to enable the housing to be latched in place or removed upwardly from the rest of the device. The latching assembly also allows, at appropriate intervals controlled by programming, the housing 60 to be pushed down in the upper half of moulding 58 to enable a set of pins 72 to press on the ends of the arms of a spider 74 and so cause the container 62 to be pressed towards the nozzle 64, so dispensing a dose of medicament therefrom. After one (or if programmed appropriately more) such compressions, the latch assembly may lock the housing 60 against further such movement until released when the next dose of medicament is due to be dispensed. The exact nature of the operation of the spider 74 and associated components is described in more detail in our copending application filed on even date and claiming the priority of GB patent application 0025811.1.

Circuit board 57 carries a display screen 76 visible through a window 78 in casing front 55. In use of the device, this screen cam carry a message to the user, for example indicating the state of the device, ready to dispense or locked. Casing front 55 also has four apertures 80 which, when the device is assembled, are filled with rubbery pressbuttons (not shown in the drawing), which enable actuation of four switches 82 set in circuit board 57. The upper end 84 of board 57 carries a printed RF antenna which enables the checking of a so-called RF tag 86 which forms part of the cartridge assembly. This enables the system to check just what medicament has been loaded into it when a fresh container 62 and associated tag 86 are inserted into the upper housing 60 and that housing latched into position in moulding 58.

The hand-held unit may be powered by a suitable battery which can fit in the area denoted 88 in the drawing.

It will be readily appreciated that using devices as shown in FIGS. 1, 4 and 5a/5b, the degree of control of dosage can be very high and the ease of recording and monitoring of the dosage regime is substantial. If, for example, the base station 2, 21 or 50 is connected into the normal telephone system, a central controlling computer can monitor the operation of the device by the user remotely, and any anomalous or undesired administration can be detected rapidly and appropriate immediate action taken. A further advantage is that, for example, a sounder is easily incorporated into the base unit which can be programmed by the central computer to emit an audible signal, e.g. to remind a user that dosage is overdue. The operating rules may provide that if within say 5 minutes of the emission of such an audible signal the user does not acknowledge having heard it, an appropriate record can be made of this event.

As noted above, the device may itself include appropriate control circuitry including a memory device. In such a case, it is possible to programme that circuitry (and a remote computer) so that when the device is first docked, it starts by establishing a communication link with the remote computer, which can then initially set-up' the device with appropriate parameters for a patient. These could, for example, govern the length of a PIN No required to access the docking station and details of the proposed dosage regime, for example initially loading an expected running average based on the prior doctor/patient experience. This false average could form the foundation for a continuing running average that is calculated with time and use. This data would constitute a benchmark, enabling the device thereafter to monitor usage levels and to detect any incidence of deviation. The time and frequency of use, and other events such as opening of the casing or tampering with it, may be stored and uploaded to a central system as desired. The system may be programmed to issue restrictive orders on the patient's medication, or it may simply be programmed to report data, so as to highlight areas of concern and alert the appropriate GP or specialist for attention at the patient's next appointment.

As noted above with reference to FIGS. 5a/5b, in place of or supplementary to the downloading of data via a remote link, data may be stored with the container for the material to be dispensed. In some areas, there is already a requirement for a form of tagging on medicinal canisters that can be read or written to. This tag carries information as to the medication type, use-by dates, etc. and when used with a device according to the present invention, the tag may be accessed by the device (and/or via the docking station), and the device could be programmed to write to the tag the number of doses left in case of removal from the device. The tag could have a large memory capacity free for other uses. On return of the canister to the pharmacist, the usage data written to the canister can then be interrogated. Data as to when the canister was used and by whom, would remain with the canister of medication that was dispensed. This method of data management may prove to be more convenient and effective in some cases than online monitoring with the device (including the canister) being mated with the docking station.

It can be seen that a wide variety of modifications may be made to the overall general construction and design described above, many of them easily made simply by changing computer programmes. Such changes could be made "online" when the hand-held unit is in the docking or base station and in communication with a host computer. The system according to the invention is of particular value in the monitoring and analysis of administration during a controlled trial, enabling it to be highly automated and reliable. In particular, detection of activity outside the instructions or constraints of the trial can be immediately and automatically achieved.

What is claimed is:

1. A dispensing system comprising a programmable dispensing mechanism adapted to receive a sealed container containing multiple doses of material to be dispensed, and including a mechanical actuation mechanism which, when actuated, causes a measured dose of material to be dispensed from the container, and wherein the dispensing mechanism is selectively inhibited from operation by a locking mechanism which, when actuated, locks the dispensing mechanism against the further dispensing of a dose of material until released in accordance with a desired dispensing programme, and wherein the container and dispensing mechanism are provided with an authenticator to check the authenticity of the container placed in the dispensing mechanism, wherein release of the locking mechanism is effected by remote control.

2. The dispensing system according to claim 1 wherein release is by the passage of sufficient time following a previous actuation.

3. The dispensing system according to claim 1 wherein release is effected by means of a latching mechanism which acts to lock the dispensing mechanism against dispensing until the latching mechanism is released.

4. The dispensing system according to claim 1 wherein the container has an identification tag associated therewith and containing information about its content, and the authenticator of the dispensing mechanism is constructed and arranged to address the tag and validate the dosage regime in accordance with the dispensing programme.

5. The dispensing system according to claim 1 wherein the dispensing mechanism is a hand-held hand-actuated dispensing mechanism including the locking mechanism and a separate base or docking station, the hand-held dispensing mechanism being constructed and arranged to be placed proximate to the base or docking station in order to release the locking mechanism.

6. The dispensing system according to claim 5 wherein the docking or base station is configured to operate in cooperation with a remote overall control system.

7. The dispensing system according to claim 5 wherein the docking or base station contains a transmitter and a receiver in communication with a remote control computer to exchange data between the remote computer and the base or docking station when the dispensing mechanism is placed in the base or docking station.

8. The dispensing system according to claim 7 wherein the dispensing mechanism is configured to upload a dispensing history of the hand-held dispensing mechanism to the remote computer in response to the remote computer sending the appropriate control signals.

9. The dispensing system according to claim 1, wherein the container is resealable.

10. The dispensing system according to claim 8, wherein the dispensing mechanism uploads the dispensing history at the same time as the remote computer sends the control signals.

11. The dispensing system according to claim 8, wherein the dispensing mechanism uploads the dispensing history after the remote computer sends the control signals.

12. The dispensing system according to claim 8, wherein the base or docking station is adapted to receive the control signals.

13. The dispensing system according to claim 8, wherein the dispensing mechanism is adapted to receive the control signals.

\* \* \* \* \*